United States Patent
Kang et al.

(10) Patent No.: US 7,763,724 B2
(45) Date of Patent: Jul. 27, 2010

(54) LIQUEFIED EXTRACT OF MARINE ALGAE FOR PRODUCING BIO-ETHANOL UNDER HIGH PRESSURE AND METHOD FOR PRODUCING THE SAME

(75) Inventors: Do Hyung Kang, Jeju-do (KR); Hyeon Yong Lee, Gangwon-do (KR); Jae Gun Han, Gangwon-do (KR); Heung Sik Park, Seoul (KR); Hyi Seung Lee, Seoul (KR); Rae Seon Kang, Gyeonggi-do (KR)

(73) Assignee: Korea Ocean Research And Development Institute, Ansan, Gyeonggi-Do (KR)

( * ) Notice: Subject to any disclaimer, the term of this patent is extended or adjusted under 35 U.S.C. 154(b) by 0 days.

(21) Appl. No.: 12/533,477

(22) Filed: Jul. 31, 2009

(65) Prior Publication Data
US 2010/0041926 A1    Feb. 18, 2010

Related U.S. Application Data

(63) Continuation of application No. PCT/KR2008/007489, filed on Dec. 17, 2008.

(30) Foreign Application Priority Data

Aug. 12, 2008  (KR) .................... 10-2008-0079138
Dec. 16, 2008  (KR) .................... 10-2008-0127852

(51) Int. Cl.
*C07H 1/00*   (2006.01)
*C07H 3/02*   (2006.01)
(52) U.S. Cl. ....................................... 536/124
(58) Field of Classification Search .................. 536/124
See application file for complete search history.

(56) References Cited

FOREIGN PATENT DOCUMENTS

JP       2007-269767 A     10/2007

OTHER PUBLICATIONS

Prospect and Future of Bio-Ethanol Using Marine Algae, Yong-jin Kim, The Membrane Society of Korea, Summer Workshop Presentation Material, Jul. 24, 2008.

*Primary Examiner*—Elvis O Price
(74) *Attorney, Agent, or Firm*—Edwards Angell Palmer & Dodge LLP; Kongsik Kim

(57) ABSTRACT

A high-pressure liquefied extract of marine algae for producing bioethanol and a method of producing the liquid extract from marine algae under high pressure, and a method of producing the bioethanol from the high-pressure liquid extract by fermentation with yeast are disclosed. According to the production method of bioethanol using marine algae, the high-pressure liquefied extract can be obtained in high yield and fermentation time can be also reduced. Consequently, the yield of bioethanol is increased. Furthermore, the method gives economical and environmentally friendly values from natural marine algae.

8 Claims, 5 Drawing Sheets

LIQUEFIED EXTRACT OF MARINE ALGAE FOR PRODUCING BIO-ETHANOL UNDER HIGH PRESSURE AND METHOD FOR PRODUCING THE SAME

CROSS REFERENCE TO RELATED APPLICATIONS

This application is a continuation, under 35 U.S.C. 111(a), of International Application No. PCT/KR2008/007489, filed on Dec. 17, 2008, which claims priority of Korean Application No. 10-2008-0079138, filed on Aug. 12, 2008, and Korean Application No. 10-2008-0127852, filed on Dec. 16, 2008, the entire contents of which are incorporated herein by reference.

BACKGROUND

1. Technical Field

The present invention relates to a high-pressure liquefied extract of marine algae for producing bioethanol under high pressure and a method of producing the same and, more particularly, to a method of producing a liquid extract from marine algae under high pressure and of producing bioethanol from the liquid extract by fermentation with yeast.

2. Background Art

Development of alternative energy has become a global topic on the background of high oil prices, energy security, and tight restriction on greenhouse gas emissions with that bioethanol supply, the next generation fuel, is under rapid development world-wide. The Bush administration proclaimed that they will increase the use of alternative energy such as bioethanol and reduce 20% of oil consumption by 2017, and Japan, China, and ASEAN nations are promoting policies on the expansion of bioethanol production.

Bioethanol is a fuel extracted from plants such as sugar cane and corn. In addition to biodiesel, bioethanol comes into the spotlight as a representative renewable energy resource because bioethanol can be used solely or mixed with gasoline as a fuel for vehicles. Moreover, bioethanol reduces dependence on imports of crude oil. Carbon dioxide emitted during combustion of bioethanol is an exception in the calculation of greenhouse gas emissions provided in the Kyoto Protocol so that reduction of greenhouse gas emissions can be achieved. Unlike any other clean fuel for which there is a need to build up infrastructure (such as a fueling station) for supply, bioethanol supply is possible with an existing infrastructure (such as a gas station), so that early commercial use of bioethanol is possible. As such, the production of bioethanol is gradually increasing with an increase of the demand and interest for bioethanol.

However, since bioethanol is emerging as an alternative energy, the demands for corn, sugar cane, and wheat which are raw material for bioethanol are rapidly increased. This is one of the factors causing the surge in grain prices.

Especially, it is expected that the use of a competitive agricultural products such as corn which is a raw material for the production of ethanol is increased, thus the production expansion of bio-fuel is causing an increased demand for corn. The expanding demand for corn is likely to cause rising costs for beverage and food makers in which grain is used as raw materials, and for cattle and poultry farmers. Consequently, it is anticipated that consumer prices of food and livestock products will increase. The method of producing bioethanol from grain cannot be free itself from the problem of the surge in grain prices as well as criticism that grain resources could be used as food for starving people.

Hereupon, the world market of bioenergy is looking to shift its source from grain ethanol to cellulosic ethanol, but lignin removal in the process for the production of cellulosic ethanol is a problem and a breakthrough related thereto has not yet been found.

Recently, some research groups at home and abroad are developing a technique producing bioethanol from carbohydrate and saccharide-rich marine algae. Marine algae has higher economic effects in harvest frequencies, crop yields per unit land area, carbon dioxide absorption power per unit land area, energy yield, and production costs per liter than other raw materials such as grain and wood, and has relatively less negative factors such as destruction of food resources and nature. When marine algae which abnormally overgrowth due to eutrophication of sea water and pollutes sea water is used as a raw material for producing bioethanol, economical and environmentally friendly advantages such as converting waste materials into value added products are expected.

Production of bioethanol requires three steps; a saccharification of a raw material, a fermentation, and a distillation. Pretreatments such as a chemical treatment, a thermal treatment, and an enzyme treatment are used in the saccharification process. However, these pretreatments have disadvantages such as a low yield, changes of components, corrosion of the equipments by additives, environmental pollution, and production of useless by-products. No results having commercial possibilities have been reported yet. Moreover, growth of yeast used in a fermentation process is inhibited by the produced alcohol so that efficiency of bioethanol production becomes inferior.

The above information disclosed in this Background section is only for enhancement of understanding of the background of the invention and therefore it may contain information that does not form the prior art that is already known in this country to a person of ordinary skill in the art.

SUMMARY OF DISCLOSURE

Therefore, the present invention has been made in view of the above problems, and the present invention provides a method for producing bioethanol from marine algae in high yield.

The present invention further provides a high pressure liquefied extract for bioethanol and a method of producing the same.

The present invention further provides a bioenergy source using marine algae which causes marine pollution due to overgrowth.

To achieve above objects, the present invention discloses a high pressure liquefied extract obtained from marine algae by the use of a high pressure liquefaction extractor and production method of the same.

In one embodiment, the present invention provides a liquefying method of marine algae at 500 to 1000 MPa. When the pressure is lower than 500 MPa, a degree of destruction of tissues is low so that an extracted quantity of glucose is reduced. Oppositely, when extraction is carried out higher than 1000 MPa, other substances in tissues are extracted. Hence, the other substances are to be removed before fermentation.

The method of the present invention is preferably carried out for 30 minutes after pressure is reached at 1000 MPa.

And a temperature of high pressure liquefied extraction is preferably 60 to 80° C. Liquefying activity is suppressed when an extraction temperature is lower than 70° C. Tissues are denatured when an extraction temperature is higher than 70° C.

In the embodiment, marine algae are brown algae, red algae, or green algae, but it is not limited to these. FIG. 3 shows a glucose yield, with time of glucose extraction after liquefaction of green algae under high pressure.

In the embodiment, water or oil is used as a pressure medium to deliver uniform pressure.

In the embodiment, alcohol is produced by fermentation of high pressure liquefied extract according to the present invention by the use of yeast.

According to the present invention, the method of producing bioethanol using marine algae is a simple process to obtain a high-pressure liquefied extract in high yield and to reduce fermentation time, so that the yield of bioethanol is increased. Although the weak acid treatment method used in general requires a long time and high costs for a treatment of byproducts after the extraction, the present invention provides a method of producing bioethanol production with low costs and in a high yield. Furthermore, when bioethanol is extracted from marine algae which could be a new biomass kwon as an environmental pollutant by overgrowth in near-shore, the method of the present invention provides economical and environmentally friendly value added products from marine wastes.

BRIEF DESCRIPTION OF DRAWINGS

The objects, features and advantages of the present invention will be more apparent from the following detailed description in conjunction with the accompanying photograph and drawings, in which:

FIG. 4 is a photograph of samples obtained by the method according to the embodiment of the present invention, wherein FIG. 4A is the high pressure liquefied extract, FIG. 4B is the fermentation broth of *Ulva pertusa*, and FIG. 4C is the distillate (bioethanol) after fermentation.

DETAILED DESCRIPTION OF EMBODIMENTS

Hereinafter, embodiments of the present invention will be described in detail. It should be understood that many variations and modifications of the basic inventive concept herein described, which may appear to those skilled in the art, will still fall within the spirit and scope of the present invention as defined in the appended claims.

In an aspect, the present invention provides a high-pressure liquefied extract of marine algae for producing bioethanol and a method of producing the same and, more particularly, to a method of producing a liquid extract from marine algae under high pressure and of producing bioethanol from the liquid extract by fermentation with yeast.

Brown algae, red algae, and green algae are used in the embodiments of the present invention, but it is neither limited to them nor to the kind of marine algae.

Water or oil is used as a pressure medium to deliver a uniform pressure during the high-pressure liquefaction performed in the embodiments of the present invention.

According to an embodiment of the present invention, *Ulva pertusa*, the most popular species in green algae is used. Recently, rapid growth of the species along the all coastal waters in Korea is one of the factors of coastal sea pollution, and the algal pollutant causes several problems such as economic and social problems in coastal area. However, dry weight of saccharide and starch in dried *Ulva pertusa* is about 50% so that it is highly useful and valuable feedstock as a raw material for bioethanol.

According to another embodiment of the present invention, brown algae (*Ecklonia cava*) and red algae (*Pachymeniopsis lanceolata* and *Gelidium elegans*) are used.

Hereinafter, the embodiments of the present invention will be described more in detail. A non-enzymatic extraction method is used in the embodiments and these embodiments are provided only for illustrative purpose and should not be interpreted as limiting the scope and spirit of the present invention.

EXAMPLES

Comparative Example 1

Glucose Extraction by Thermal Treatment of *Ulva pertusa*

*Ulva pertusa* was placed in a flask fitted with a vertical reflux condenser and then extracted twice with 10 times distilled water at 100° C. for 24 hours.

Comparative Example 2

Glucose Extraction by Weak Acid Treatment of *Ulva pertusa*

*Ulva pertusa* was placed in a flask fitted with a vertical reflux condenser and then extracted with 10 times 1% sulfuric acid solution at 123° C. for 1 hour.

Example 1

Glucose Extraction by High-Pressure Liquefaction of *Ulva pertusa*

Figure 1:
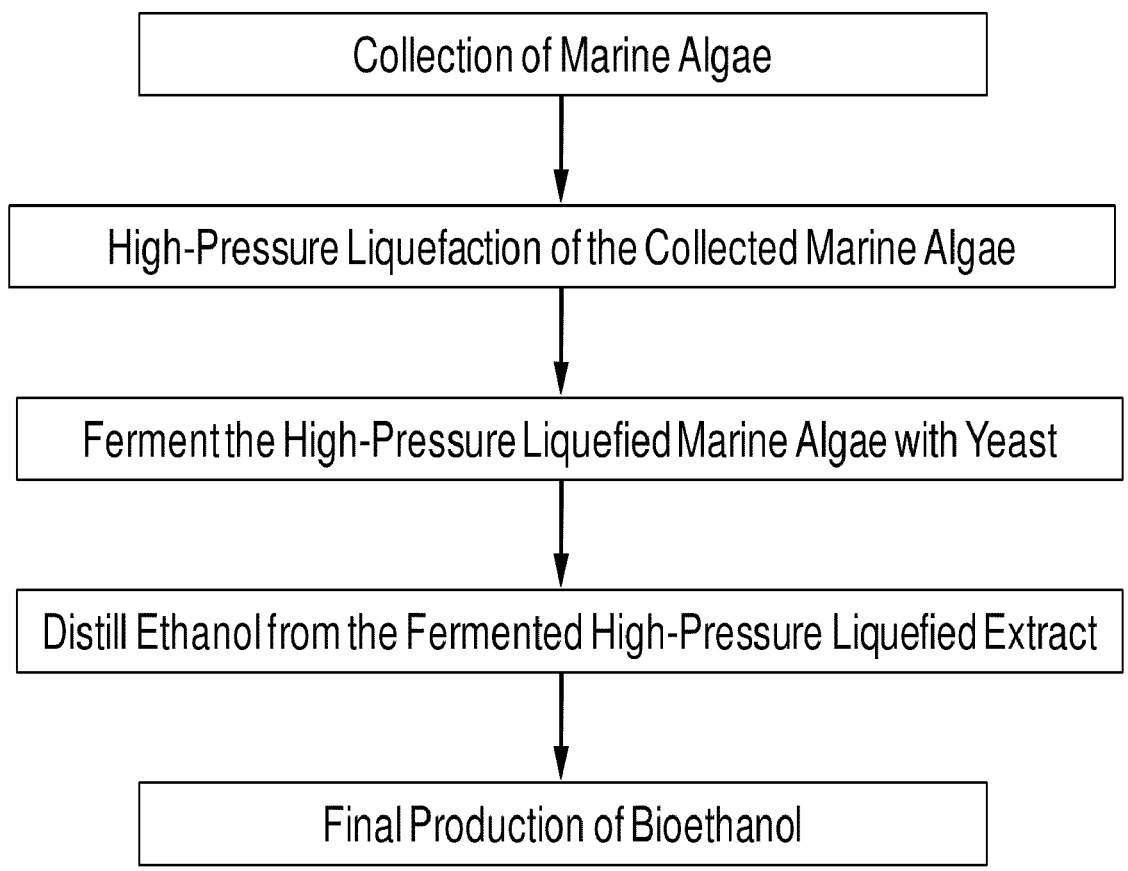
FIG. 1 is a flowchart illustrating a method of producing bioethanol from marine algae according to an embodiment of the present invention.
Figure 2:
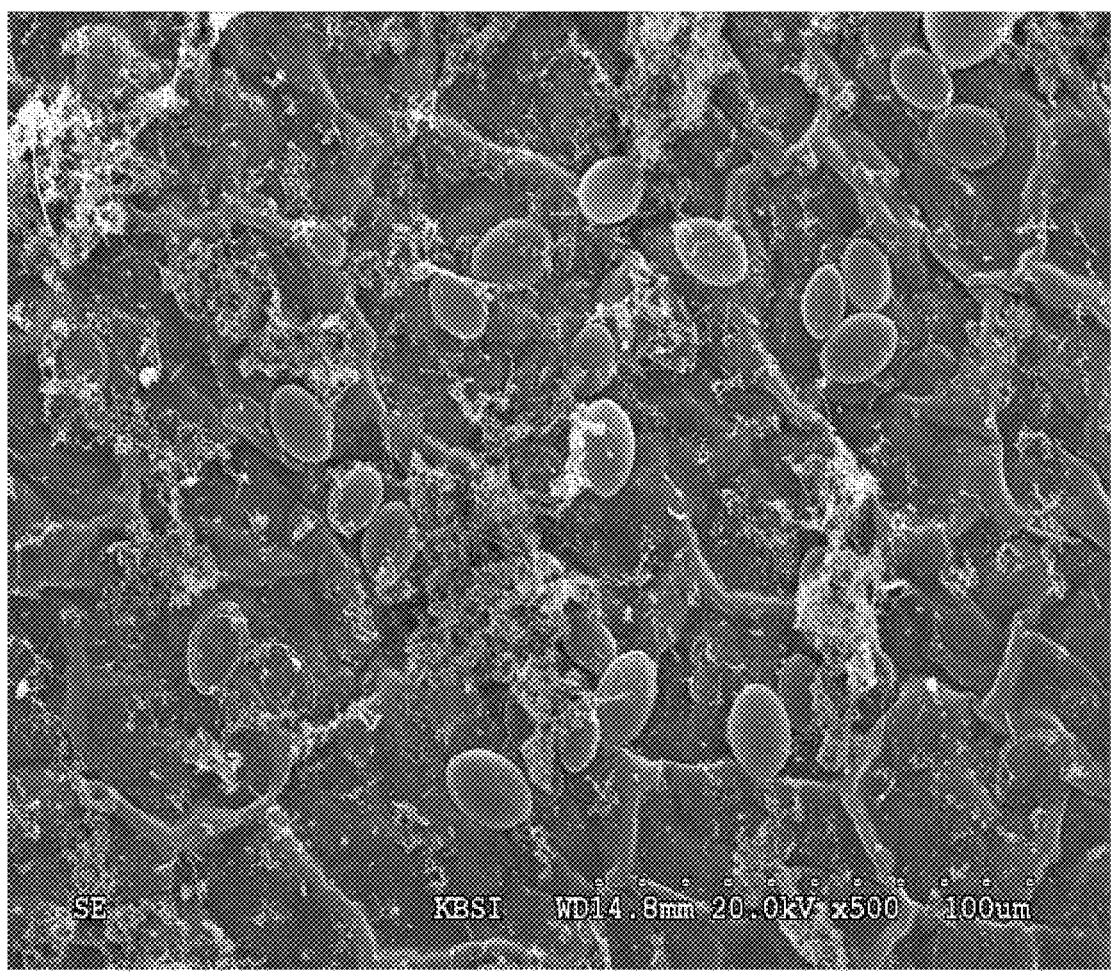
FIG. 2 is a scanning electron microscope photograph of a surface morphology of *Ulva pertusa* after high-pressure liquefaction performed according to the embodiment of the present invention.
Figure 3:
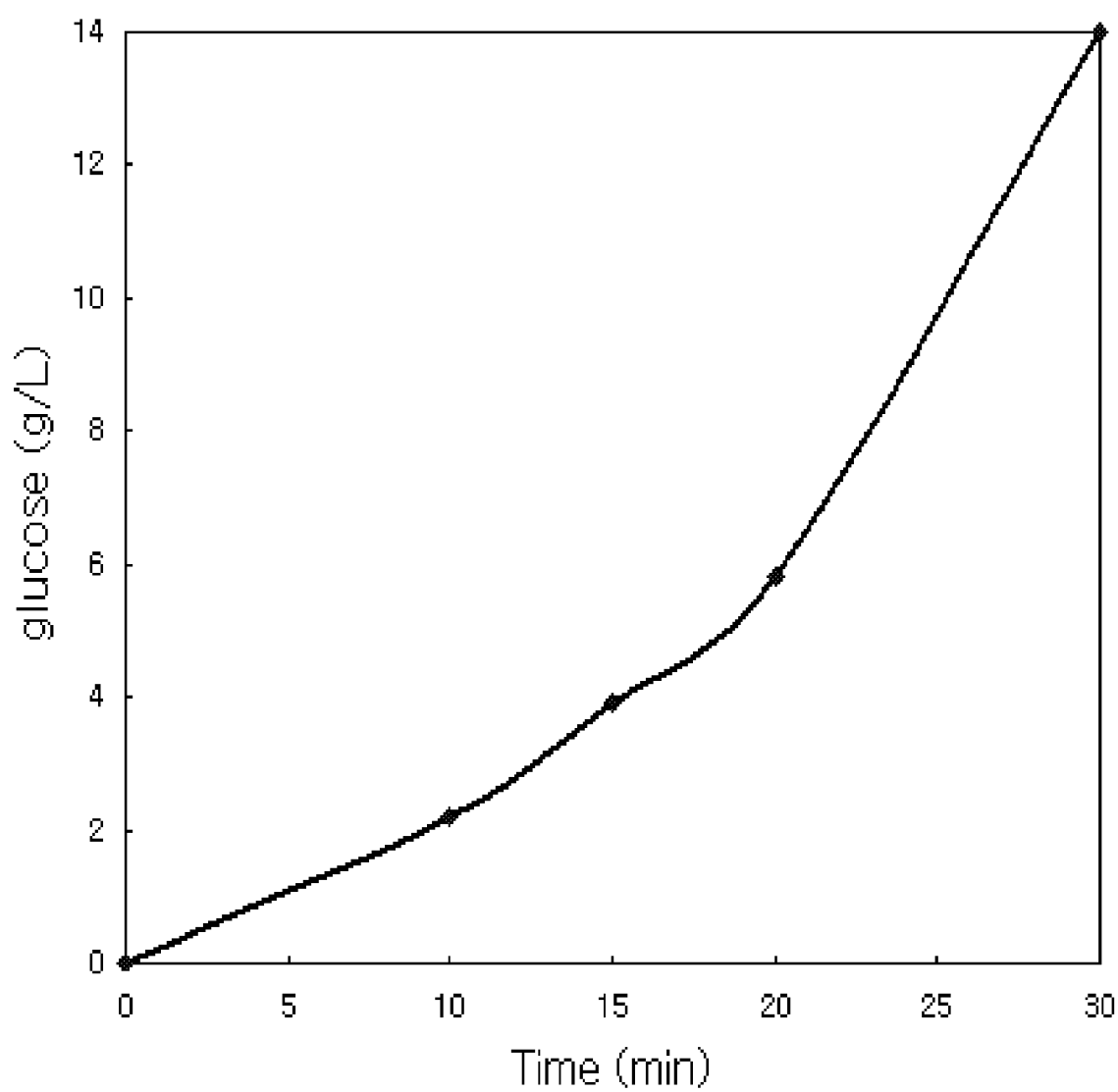
FIG. 3 is a graph illustrating a glucose yield, with time of glucose extraction after the high-pressure liquefaction of green algae according to the embodiment of the present invention.

A 100 g of *Ulva pertusa* was placed in a high-pressure liquefaction extractor with water as a pressure medium and then pressure was increased from 500 MPa to 1000 MPa at 70° C., and the pressure was maintained at 1000 Mpa for 30 minutes. After finishing the extraction, the break-downed cells of *Ulva pertusa* was shown in FIG. 2. As shown in surface morphology photograph (FIG. 2), the tissue of *Ulva pertusa* was homogenized completely after the high-pressure liquefaction.

Measurement of Extracted Glucose Content (DNS Method)

The contents of glucose in comparative examples 1 and 2, and example 1 which were measured by DNS method are as follows in Table 1.

TABLE 1

|  | Comparative example 1 | Comparative example 2 | Example 1 |
|---|---|---|---|
| Glucose (g/L) | 3.01 | 9.80 | 14.0 |

As listed in table 1, example 1 of the present invention is a simple process and resulted in 1.4-4.7 times higher yield than that a traditional glucose extraction methods. Considering that total content of glucose in *Ulva pertusa* is about 20% (w/w), extraction and saccharification yields of over 20% is increased by the high-pressure liquefaction process in example 1.

Example 2

Cultivation of Yeast for Alcohol Fermentation

The yeast for alcohol fermentation (*Saccharomyces cerevisiae*, Aden Forbes Lab, Bakers Yeast, 4330910) is used to confirm a possibility of alcohol fermentation of a high-pressure liquefied extract and a growth inhibition of a yeast during saccharification. The high-pressure liquefied extract (10~35% v/v) in 500 mL was fermented in a yeast extract culture medium.

Example 3

Production of Bioethanol from Green Algae *Ulva pertusa*

The high-pressure liquefaction extract of *Ulva pertusa* obtained in example 1 was fermented with yeast of example 2, and then the mixture was distilled to produce bioethanol. The high-pressure liquefied extract was placed in a bioengineering system and then fermented at 25° C. at 80 rpm. The alcohol fermentation was carried out under an anaerobic condition. The mixture was stirred intermittently for maintaining an anaerobic or micro-aeration condition during the fermentation so as to maintain a certain concentration of yeast in a culture medium. The same subsample of broth was collected in a certain interval, and stored in a refrigerator at 4° C. These subsamples were centrifuged and then supernatants were used for the quantitative analysis of the produced alcohol. Gas chromatography (HP 5890-II, porapak Q column) equipped with a thermal conductivity detector and thin layer chromatography (TLC) was used for the analysis.

Figure 4:
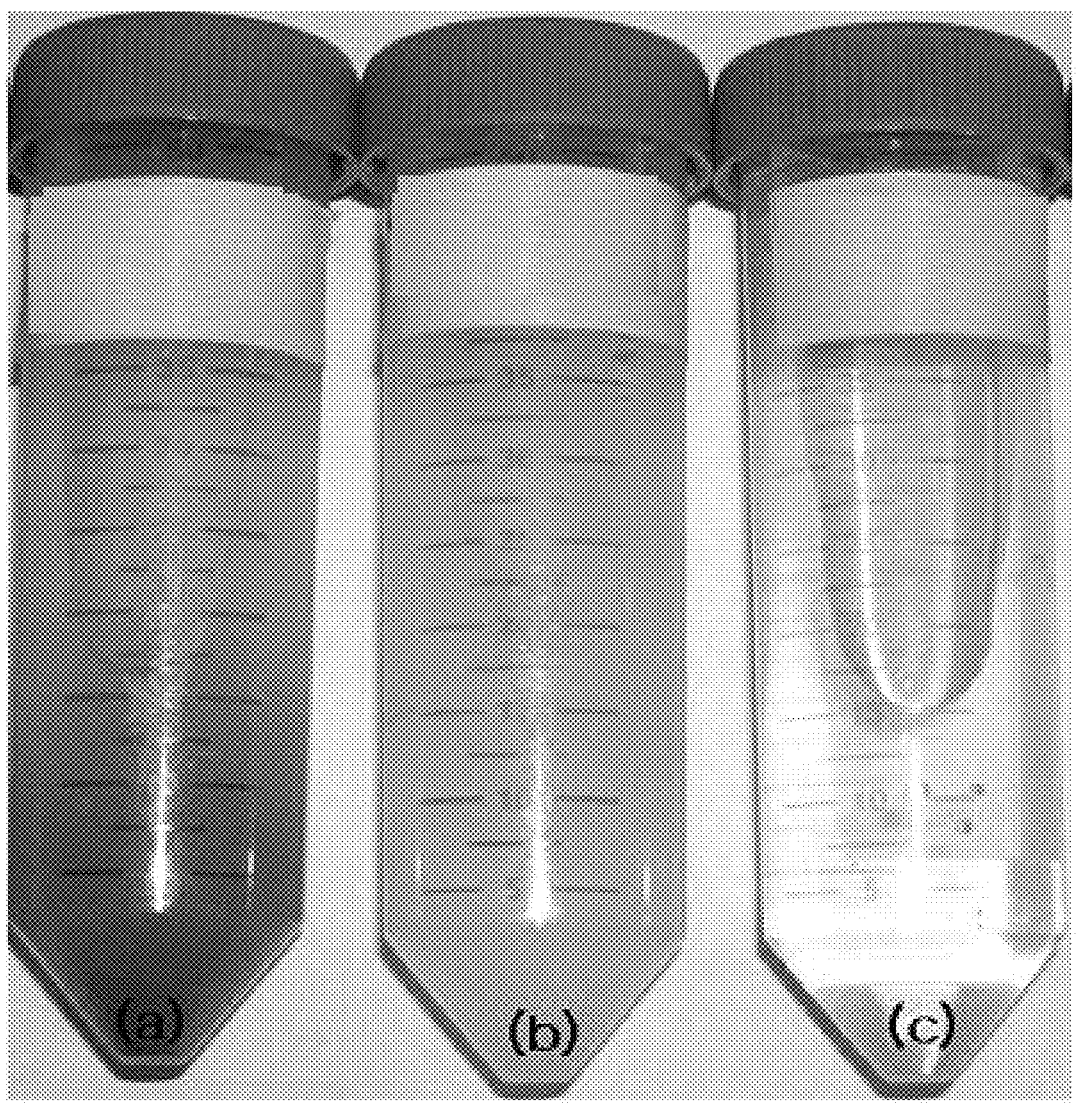

FIG. 4 is a photograph illustrating samples obtained in ethanol production steps according to the embodiment of the present invention, wherein FIG. 4A is the high-pressure liquefied extract, FIG. 4B is the fermentation broth of *Ulva pertusa,* and FIG. 4C is the distillate (bioethanol) after fermentation.

Figure 5:
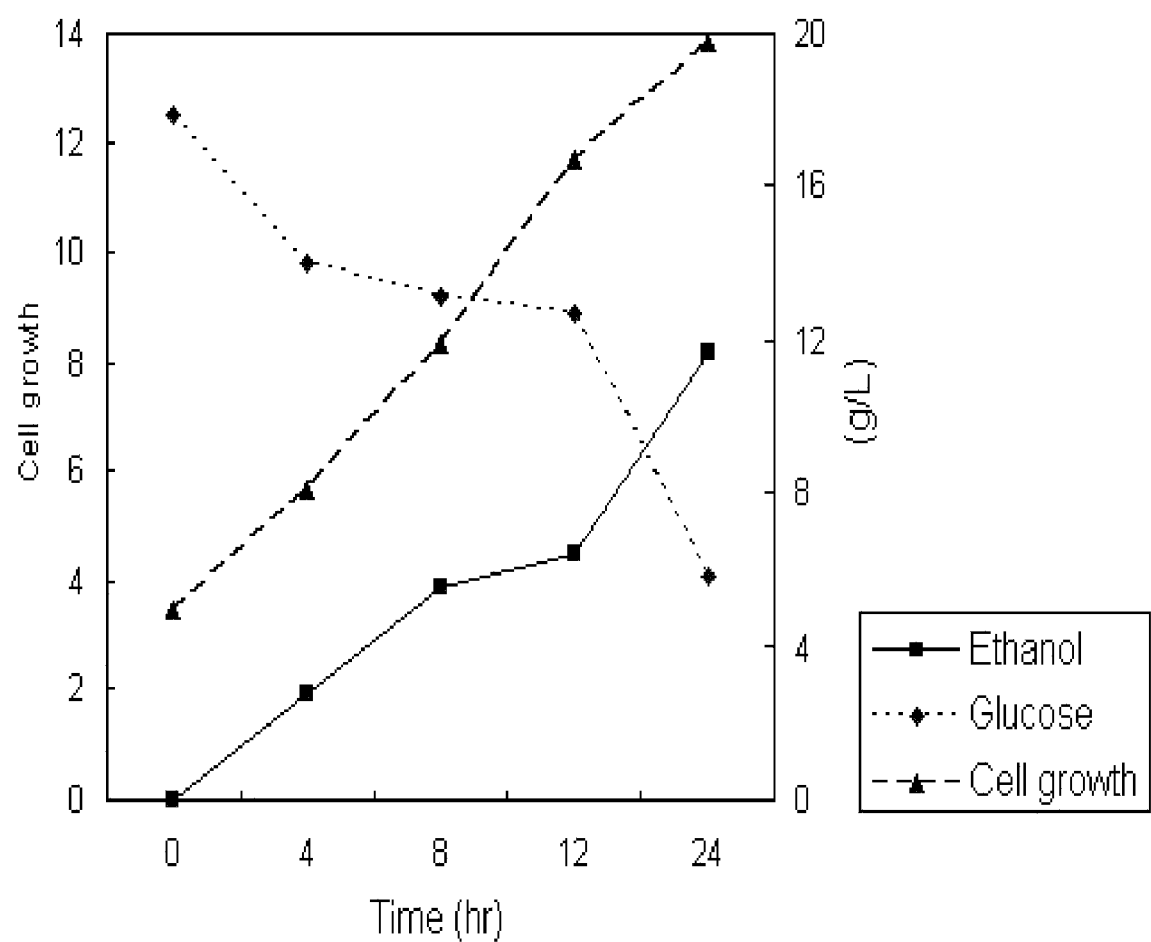
FIG. 5 is a graph illustrating a concentration of glucose consumption, a concentration of ethanol production, and yeast growth with time of fermentation according to the method of the embodiment of the present invention.

Table 2 shows concentrations of produced ethanol obtained in example 3. FIG. 5 is a graph illustrating a concentration of glucose consumption, a concentration of ethanol production, and yeast growth with time during fermentation, which are obtained in example 3.

TABLE 2

| Time (hr) | Ethanol/ Butanol | Ethanol (%, v/v) | Ethanol (%, w/v) | Ethanol (%, g/L) |
|---|---|---|---|---|
| 0 | — | — | — | — |
| 4 | 0.35 | 0.46 | 0.36 | 3.69 |
| 8 | 1.63 | 1.71 | 1.35 | 13.52 |
| 12 | 2.60 | 2.65 | 2.09 | 20.96 |
| 24 | 3.38 | 3.41 | 2.69 | 26.95 |

As shown in FIG. 5, when the high-pressure liquefied extract of *Ulva pertusa* was fermented with yeast, the fermentation was finished within 24 hours and ethanol was continually produced. Since a quantity of remaining glucose was continually decreased in proportion to the production of ethanol, it is understood that glucose extracted from *Ulva pertusa* can be used for yeast growth and the ethanol fermentation.

Example 4

Comparative Experiment Regarding Glucose Conversion Yield of Brown Algae *Ecklonia cava*

Brown algae *Ecklonia cava* (1 g in dried weight) instead of *Ulva pertusa* was used for glucose extraction performed by the method of example 1. For comparison, glucose conversion yield in the method of comparative example 2 was measured. For reference, carbohydrate content in brown algae *Ecklonia cava* was 28.9% (w/w) and glucose content was 15.7% (w/w). The following Table 3 shows results of an acid treatment of *Ecklonia cava* and of glucose conversion yield obtained by the method of example 1.

TABLE 3

| Species | Acid treatment | Method of the example 1 |
|---|---|---|
| *Ecklonia cava* | 5.8 | 6.4 |

Example 5

Ethanol Production from Brown Algae *Ecklonia cava*

Bioethanol was produced by the method according to example 3 from the sample obtained in example 4. As a result, the maximum alcohol content was 2.8% (v/v) and about 78% of alcohol was produced in comparison with the existing glucose in the liquid. When the alcohol fermentation yield from 1 mole of glucose is about 50%, the result approaches the maximum theoretical yield of 3.2% (v/v).

Example 6

Comparative Experiment Regarding Glucose Conversion Yield of Red Algae *Pachymeniopsis lanceolata* and *Gelidium elegans*

Red algae, *Pachymeniopsis lanceolata* (1 g in dry weight) and *Gelidium elegans* (1 g in dry weight) were used for glucose extraction by the method of example 1. For comparison, glucose conversion yield by the method of comparative example 2 was measured. For reference, carbohydrate contents of red algae *Pachymeniopsis lanceolata* and *Gelidium elegans* were 60.1 and 51.3% (w/w) respectively and glucose contents were 45.9 and 15.3% (w/w) respectively. The following Table 4 shows the results of acid treatments and glucose conversion yields obtained by the method of example 1.

TABLE 4

| Species | Acid treatment method | Method of example 1 |
|---|---|---|
| *Pachymeniopsis lanceolata* | 15.6 | 25.3 |
| *Gelidium elegans* | 4.9 | 7.3 |

Example 7

Ethanol Production from Red Algae *Pachymeniopsis lanceolata* and *Gelidium elegans*

Bioethanol was produced from the samples obtained in example 6 and by the method according to example 3. As a result, the maximum alcohol contents are 9.4% (v/v) from *Pachymeniopsis lanceolata* and 2.4% (v/v) from *Gelidium elegans,* and 74% and 65% of alcohol was produced respectively in comparison with the existing glucose in the liquid. When the alcohol fermentation yield from 1 mole of glucose is about 50%, the results approach the maximum theoretical yields of 12.7% (v/v) from *Pachymeniopsis lanceolata* and 3.7% (v/v) from *Gelidium elegans*.

As listed in the tables 3 and 4, the method according to the embodiments of the present invention gives a glucose conversion yield higher than that of the acid treatment method. This simple high-pressure liquefaction is more useful and reliable method for considerations on mitigation of green tidal problems, and costs for the acid treatment, and the complicated manufacturing process using conventional methods. After the fermentation of the produced samples, the yield of ethanol was about 80% in comparison with the maximum theoretical conversion yield of existing glucose in a liquid. The yield was higher than the reported yields of ethanol fermentation of treated cellulose products. Moreover the high-pressure liquefied extract was useful for yeast growth.

As described above, the method of producing bioethanol using marine algae according to the present invention is a simple process to obtain a high-pressure liquefied extract in high yield and to reduce fermentation time, so that the yield of bioethanol is increased. Although the weak acid treatment method used in general requires a long time and high costs for a treatment of byproducts after the extraction, the present invention provides a method of producing bioethanol production with low costs and in a high yield. Furthermore, the method of the present invention gives economical and environmentally friendly values added products from wastes when bioethanol is extracted from green algae which could be a new biomass known as an environmental pollutant by overgrowth in seashore.

Although embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method of liquefying marine algae by increasing pressure ranged from 500 MPa to 1000 MPa.

2. The method of the claim 1, wherein a liquefying temperature is in the range of 60 to 80° C.

3. The method of the claim 1, wherein a pressure medium is selected from water or oil.

4. The method of the claim 1, wherein the algae are selected from the group consisting of green algae, brown algae and red algae.

5. The method of the claim 4, wherein the marine algae is *Ulva pertusa*.

6. The method of the claim 4, wherein the marine algae is *Ecklonia cava*.

7. The method of the claim 4, wherein the marine algae is *Pachymeniopsis lanceolata*.

8. The method of the claim 4, wherein the marine algae is *Gelidium elegans*.

* * * * *